(12) United States Patent
Wilkinson et al.

(10) Patent No.: US 11,554,119 B2
(45) Date of Patent: Jan. 17, 2023

(54) COMPOSITION HAVING IMPROVED FLOWABILTY AND METHODS FOR MAKING AND USING THE COMPOSITION

(71) Applicant: Phibro Animal Health Corporation, Teaneck, NJ (US)

(72) Inventors: Ian John Wilkinson, Teaneck, NJ (US); Charles Hollett Fahrenholz, Teaneck, NJ (US)

(73) Assignee: Phibro Animal Health Corporation, Teaneck, NJ (US)

( * ) Notice: Subject to any disclaimer, the term of this patent is extended or adjusted under 35 U.S.C. 154(b) by 411 days.

(21) Appl. No.: 16/665,841

(22) Filed: Oct. 28, 2019

(65) Prior Publication Data

US 2020/0054631 A1 Feb. 20, 2020

Related U.S. Application Data

(63) Continuation of application No. PCT/US2018/039569, filed on Jun. 26, 2018.

(60) Provisional application No. 62/526,775, filed on Jun. 29, 2017.

(51) Int. Cl.
| | |
|---|---|
| *A61K 31/505* | (2006.01) |
| *A23K 20/137* | (2016.01) |
| *A23K 10/30* | (2016.01) |
| *A61P 1/00* | (2006.01) |
| *A61K 9/16* | (2006.01) |
| *A61K 36/899* | (2006.01) |
| *A61K 47/44* | (2017.01) |

(52) U.S. Cl.
CPC ............ *A61K 31/505* (2013.01); *A23K 10/30* (2016.05); *A23K 20/137* (2016.05); *A61K 9/1611* (2013.01); *A61K 36/899* (2013.01); *A61K 47/44* (2013.01); *A61P 1/00* (2018.01)

(58) Field of Classification Search
CPC .. A61K 31/505; A61K 9/1611; A23K 20/137; A61P 1/00
See application file for complete search history.

(56) References Cited

U.S. PATENT DOCUMENTS

| 5,629,038 A | 5/1997 | Kalmbach |
| 2004/0013613 A1 | 1/2004 | Jain et al. |
| 2006/0018979 A1 | 1/2006 | Hafermann et al. |
| 2016/0235093 A1 | 8/2016 | Brion et al. |

FOREIGN PATENT DOCUMENTS

| EP | 0 060 680 | 9/1982 |
| EP | 0 171 628 | 2/1986 |
| EP | 0 217 631 | 4/1987 |
| FR | 2 909 5 5 8 | 6/2008 |
| WO | WO 92/08373 | 5/1992 |

OTHER PUBLICATIONS

Corrigan et al., "The Use of Microtracers in a Medicated Premix to Determine the Presence of Tiamulin in Final Feed", Drug Development and Industrial Pharmacy, vol. 20, No. 8, pp. 1503-1509 (1994).*
International Search Report dated Oct. 10, 2018 from International Application No. PCT/US2018/039569 (6 pages).
Written Opinion dated Oct. 10, 2018 from International Application No. PCT/US2018/039569 (10 pages).

* cited by examiner

*Primary Examiner* — Kevin E Weddington
(74) *Attorney, Agent, or Firm* — Klarquist Sparkman, LLP

(57) ABSTRACT

Disclosed compositions comprise a therapeutic agent and a carrier selected, or processed to have, an acceptable composite flow index, a granular particle size of 18 mesh to 80 mesh, or both, such as processed granular wheat middlings. The composition may also comprise an oil and/or micro tracers. Suitable granular wheat middlings may have a size range of from 18 mesh to 80 mesh, such as 20 mesh to 80 mesh. The composition has improved flowability characteristics, compared to a composition where the carrier, such as processed wheat middlings, are powdered and/or flakey. Certain embodiments concern a composition comprising, consisting essentially of, or consisting of, nicarbazin, granular wheat middlings, soybean oil and micro tracers. The composition may be administered to an animal, for example, to treat or prevent coccidiosis. Also disclosed herein are methods for making and using the composition.

9 Claims, 3 Drawing Sheets

COMPOSITION HAVING IMPROVED FLOWABILTY AND METHODS FOR MAKING AND USING THE COMPOSITION

CROSS REFERENCE TO RELATED APPLICATIONS

This application is a continuation of International Application No. PCT/US2018/039569, filed on Jun. 26, 2018, which claims the benefit of U.S. Provisional Application No. 62/526,775, filed Jun. 29, 2017, which is herein incorporated by reference in its entirety.

FIELD

This invention concerns a therapeutic composition, particularly a therapeutic composition having improved flowability, a therapeutic composition comprising processed wheat middlings, or both, such as a nicarbazin composition comprising processed wheat middlings and having improved flowability, and methods for making and administering the composition to animals.

BACKGROUND

Formulations comprising wheat middlings and a therapeutic agent typically are powders or comprise flaky components. These compositions often have deleterious flowability issues, such as, for example, when used with automated machinery, including automated weighing machines and feed mills. Exemplary flowability issues include "surge flow" or "bridge over" during conveyance and/or pouring. "Surge flow" occurs when powdered and/or flakey compositions do not flow evenly, but rather flow in waves. An amount of the powdered and/or flakey composition will accumulate as a result of differential flow along a flow path, followed by a surge flow or flood of composition downstream along the flow path. "Bridge over" typically occurs when a powdered and/or flakey composition does not pass through an opening, such as an outlet or inlet in a container, but instead jumps or bridges over the opening. Bridge over may be caused, at least in part, by electrical charges on the particles, which results in mutual particle repulsion and/or attraction to the container's walls and sides of the opening.

Flowability issues may occur for a number of therapeutic compositions, such as nicarbazin compositions. Nicarbazin is administered to prevent and/or treat parasitic infections, such as coccidiosis in poultry. Prior attempts have been made to address flowability issues for certain nicarbazin compositions, including agitating the composition, such as by stirring or using rotating balls in the hoppers. However, these attempts have not successfully addressed the flowability problems.

SUMMARY

Disclosed herein are embodiments of a composition having improved flowability properties. For example, disclosed nicarbazin formulations have improved flowability characteristics, but the changed flowability characteristics do not change the composition nor deleteriously affect the activity or efficacy of the nicarbazin formulation, compared to current powdered and/or flakey formulations.

Certain disclosed embodiments concern a composition comprising a therapeutic agent and processed granular wheat middlings having a size of from 20 mesh to 80 mesh, a beneficial change in carrier composite flow index, such as a change of 30% to 200%, or both. The composition may further comprise additional beneficial additives, such as an oil, including mineral oil, soybean oil, or a combination thereof, and/or micro tracers. In some embodiments, the composition comprises from 1 wt % to 10 wt % oil, from 10 wt % to 50 wt % therapeutic agent, and from 40 wt % to 90 wt % wheat middlings.

The therapeutic agent may be any therapeutic now known or hereafter developed, particularly those formulated with wheat middlings, such as amprolium, avilamycin, bacitracin methylene disalicylate (bmd), zinc bacitracin, bambermycin, carbadox, ceftiofur, chlortetracycline, clopidol, decoquinate, diclazuril, dihydrostreptomycin, enrofloxacin, erythromycin, fenbendazole, flavomycin, florfenicol, gentamicin, sulphadimidine, ivermectin, laidlomycin, lasalocid, lincomycin, maxiban, meduramicin ammonium, monensin, morantel tartrate, narasin, neomcyin sulfate, nicarbazin, niclosamide, oxytetracycline, penicillin, poloxalene, pyrantel tartrate, ractopamine, robenidine, roxarsone, salinomycin, semduramicin, spectinomycin, stenerol, sulphadimidine, sulfadimethoxine, terramycin, neo-terramycin, tetracycline, tiamulin, tilmicosin, thiabendazole, toltrazuril, trimethoprim, tulathromycin, tylosin, virginamycin, zoalene, or any combination thereof. For particular disclosed embodiments, the therapeutic agent is or comprises nicarbazin.

Particular disclosed nicarbazin formulations comprise granular wheat middlings, particular wheat middlings processed to have a size of from 20 mesh to 80 mesh, soybean oil, nicarbazin, and micro tracers. The composition may comprise, consist essentially of, or consist of, from 2 wt % to 4 wt % soybean oil, from 10 wt % to 30 wt % nicarbazin, from greater than zero to 1 wt % micro tracers, and from 65 wt % to 88 wt % granular wheat middlings. In certain embodiments, disclosed nicarbazin compositions consist of 0.5 wt % micro tracers, 25 wt % nicarbazin, 3 wt % soybean oil, with the remainder being granular wheat middlings.

In any embodiments, the granular wheat middlings may have: an angle of repose of from greater than zero to 40; a percent compressibility of from zero to 20%; a critical orifice diameter of from greater than zero to 15; and/or a composite flow index of from greater than 45 to 100. In certain embodiments, the granular wheat middlings have an angle of repose of from 30 to 40, a percent compressibility of from 15% to 20%, a critical orifice diameter of from 3 to 8, and a composite flow index of from 70 to 100, such as from 70 to 85.

In any embodiments, the composition may have: an angle of repose of from greater than zero to 40; a percent compressibility of from zero to 20%; a critical orifice diameter of from greater than zero to 30; and/or a composite flow index of from greater than 45 to 100. In some embodiments, the composition has an angle of repose of from 30 to 40, a percent compressibility of from 10% to 20%, a critical orifice diameter of from 20 to 30, and a composite flow index of from 55 to 60. In some embodiments, the composition comprising the disclosed granular wheat middlings has a composite flow index from 30% to 200% greater, such as from 50% to 150% greater, than a comparable composition comprising non-processed, powdered and/or flaky wheat middlings in place of the granular wheat middlings.

The composition may also comprise a feed, a feed supplement, or a combination thereof. The feed may comprise corn, soybean meal, soybean oil, wheat, barley, rye, rice hulls, canola, corn oil, limestone, salt, such as sodium chloride, distillers dried grains with solubles (DDGS), dicalcium phosphate, sodium sesquicarbonate, methionine source, lysine source, L-threonine, mineral oil, biotin, folic acid, kelp, menadione dimethylpyrimidinol bisulfate, calcium aluminosilicate, or any combination thereof. The feed supplement may comprise *yucca, quillaja*, or both *yucca* and *quillaja*. The *yucca* may comprise *Yucca aloifolia, Yucca angustissima, Yucca arkansana, Yucca baccata, Yucca baileyi, Yucca brevifolia, Yucca campestris, Yucca capensis, Yucca carnerosana, Yucca cernua, Yucca coahuilensis, Yucca constricta, Yucca decipiens, Yucca declinata, Yucca de-smetiana, Yucca elata, Yucca endlichiana, Yucca faxoniana, Yucca filamentosa, Yucca filifera, Yucca flaccida, Yucca gigantean, Yucca glauca, Yucca gloriosa, Yucca grandiflora, Yucca harrimaniae, Yucca intermedia, Yucca jaliscensis, Yucca lacandonica, Yucca linearifolia, Yucca luminosa, Yucca madrensis, Yucca mixtecana, Yucca necopina, Yucca neomexicana, Yucca pallida, Yucca periculosa, Yucca potosina, Yucca queretaroensis, Yucca reverchonii, Yucca rostrata, Yucca rupicola, Yucca schidigera, Yucca schottii, Yucca sterilis, Yucca tenuistyla, Yucca thompsoniana, Yucca treculeana, Yucca utahensis, Yucca valida* or a combination thereof. And/or the *quillaja* may comprise *Quillaja brasiliensis, Quillaja lanceolata, Quillaja lancifolia, Quillaja molinae, Quillaja petiolaris, Quillaja poeppigii, Quillaja saponaria, Quillaja sellowiana, Quillaja smegmadermos* or a combination thereof. In some embodiments, the *yucca* is or comprises *Yucca schidigera*, and/or the *quillaja* is or comprises *Quillaja saponaria*.

Additionally, or alternatively, the feed supplement may comprise silica, mineral clay, glucan, mannans, or a combination thereof. The feed supplement may comprise silica, mineral clay, glucan and mannans, such as 1-40 wt % silica, 0.5-25 wt % glucan and mannans, and 40-92 wt % mineral clay, in amounts relative to each other. The feed supplement may further comprise an endoglucanohydrolase, such as from 0.025 wt % endoglucanohydrolase to 5 wt % endoglucanohydrolase. The endoglucanohydrolase may be β-1,3 (4)-endoglucanohydrolase. Glucan, mannans and/or endoglucanohydrolase may be provided by yeast or a yeast wall extract.

Also disclosed are embodiments of a method of preparing a therapeutic composition having improved flowability. Certain disclosed embodiments comprise forming a blended mixture comprising a therapeutic agent, such as nicarbazin, and a processed carrier, such as granular wheat middlings processed to have a size of from 20 mesh to 80 mesh. The method may comprise forming a blended mixture of a processed carrier, such as processed granular wheat middlings, the therapeutic agent, soybean oil and micro tracers.

Appropriate granular wheat middlings may be prepared by a method comprising pelleting wheat middlings to form pellets. The pellets are milled to produce processed wheat middlings. The milled wheat middlings are sorted to purposefully select granular wheat middlings having a size of from 20 mesh to 80 mesh from oversized and/or undersized particles.

In any embodiments, forming the blended mixture may comprise forming a first mixture comprising appropriate wheat middlings and an oil. The first mixture may be mixed, such as by stirring, for a first period of time suitable to provide an intimate mixture of the wheat middlings and oil. The first period of time may be from greater than zero to 10 minutes or more, such as from 1 minute to 7 minutes, or from 3 minutes to 5 minutes. A therapeutic agent is then added to the first mixture to form the blended mixture. Adding the therapeutic agent may comprise adding the therapeutic agent to the first mixture to form a second mixture, and mixing the second mixture for a second period of time suitable to form the blended mixture. The second period of time may be selected to minimize attrition of the granular wheat middlings, such as from greater than zero to 30 minutes or more, from 5 minutes to 25 minutes, or from 10 minutes to 20 minutes.

Additionally, or alternatively, the method may comprise admixing the blended mixture with a feed, a feed supplement, or a combination thereof, to form an admixture. The feed supplement may comprise silica, mineral clay, glucan, mannans, or a combination thereof, and/or the feed supplement may comprise *yucca, quillaja*, or a combination thereof.

A method for using the composition is also disclosed. Certain embodiments concern administering an effective amount of the disclosed composition to any animal to whom disclosed compositions may be beneficially administered, including a land animal, an aquatic animal, an avian, or an amphibian, preferably an avian. The avian may be a chicken, turkey, goose, duck, Cornish game hen, quail, partridge, pheasant, guinea-fowl, ostrich, emu, swan, or pigeon, particularly a chicken or a turkey.

The method may further comprise administering a second therapeutic agent, a vaccine, a feed, a feed supplement, or a combination thereof. The second therapeutic agent, the vaccine, the feed, the feed supplement, or a combination thereof, and the disclosed composition may be administered substantially simultaneously, or alternatively, they may be administered sequentially in any order. The second therapeutic agent may be, for example and without limitation, an antimicrobial, an anticoccidial, or a combination thereof.

Additionally, a method of treating or preventing coccidiosis in an animal is disclosed, comprising administering to the animal an effective amount of a composition comprising a carrier processed to have an appropriate composite flow index, such as granular wheat middlings having a size of from 20 mesh to 80 mesh, an oil, such as soybean oil, nicarbazin, and micro tracers. The composition may comprise, consist essentially of, or consist of, from 2 wt % to 4 wt % oil, such as soybean oil, from 10 wt % to 30 wt % nicarbazin, from greater than zero to 1 wt % micro tracers, and from 65 wt % to 88 wt % wheat middlings. In certain embodiments, the composition consists of 0.5% micro tracers, 25% nicarbazin, 3% soybean oil, with the remainder being granular wheat middlings.

In some embodiments, the method comprises selecting an animal at risk of developing coccidiosis, and administering an effective amount of the composition to the animal. In particular embodiments the animal is a chicken or a turkey. The composition may be admixed with a feed prior to administration to form an admixed composition. Admixing the composition may comprise admixing a sufficient amount of the composition to form an admixed composition comprising from 60 g nicarbazin/ton of feed to 113 g nicarbazin/ton of feed.

Also disclosed is a system designed to produce compositions according to the present invention. Certain disclosed embodiments comprise a pellet mill suitable for forming a pelletized carrier, such as pelletized wheat middlings, a roller mill suitable for milling the pelletized carrier, such as wheat middlings milled to form granular wheat middlings having a size of from 20 mesh to 80 mesh, and a mixer comprising a carrier inlet and a therapeutic agent inlet. The mixer blends the carrier and the therapeutic agent to form a blended composition. A disclosed wheat middlings roller mill is configured to mill pelletized wheat middlings into granular wheat middlings having a composite flow index of from 75 to 100. The blended composition may further comprise an oil, and for these embodiments the mixer may comprise an oil inlet that optionally may comprise a sprayer. Additionally or alternatively the blended composition may comprise micro tracers, and for these embodiments the mixer may comprise a micro tracer inlet.

The foregoing and other objects, features, and advantages of the invention will become more apparent from the following detailed description, which proceeds with reference to the accompanying figures.

DETAILED DESCRIPTION

I. Definitions

Figure 1:
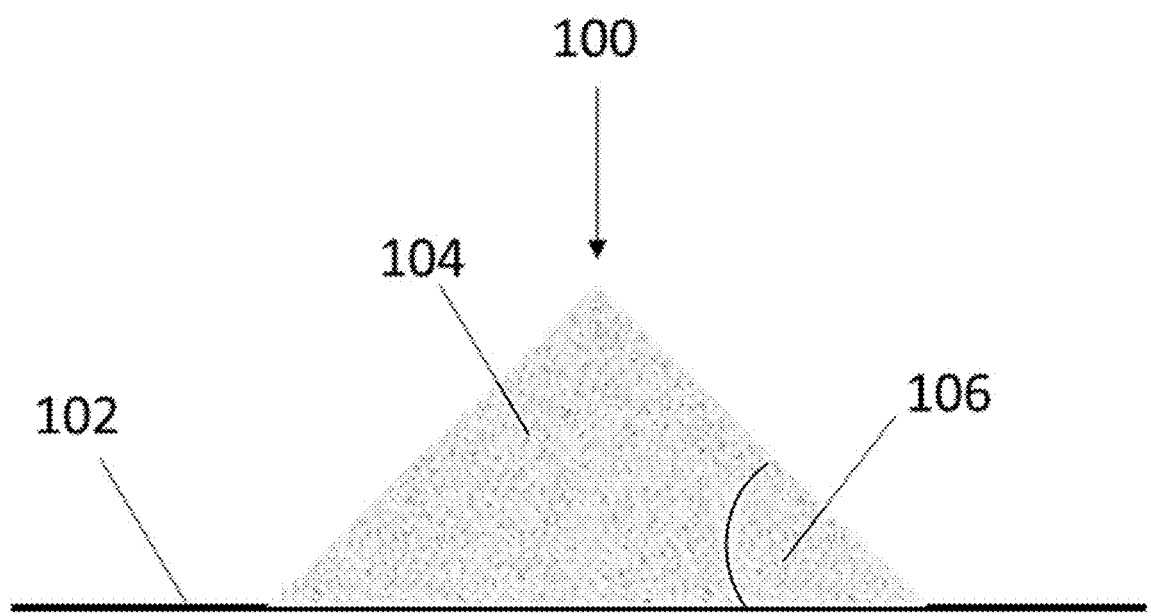
FIG. 1 is a schematic diagram illustrating one embodiment of a method for determining the angle of repose.

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Combination: A combination includes two or more components that are administered such that the effective time period of at least one component overlaps with the effective time period of at least one other component. A combination, or a component thereof, may be a composition. In some embodiments, the effective time periods of all components administered overlap with each other. In an exemplary embodiment of a combination comprising four components, the effective time period of the first component administered may overlap with the effective time periods of the second, third and/or fourth components, but the effective time periods of the second, third and/or fourth components independently may or may not overlap with one another. In another exemplary embodiment of a combination comprising four components, the effective time period of the first component administered overlaps with the effective time period of the second component, but not that of the third or fourth; the effective time period of the second component overlaps with those of the first and third components; and the effective time period of the fourth component overlaps with that of the third component only. A combination may be a composition comprising all the combination components, a composition comprising one or more components and another separate component (or components) or composition(s) comprising the remaining component(s), or the combination may be two or more individual components. In some embodiments, the two or more components may comprise the same component administered at two or more different times, two or more different components administered substantially simultaneously or sequentially in any order, or a combination of sequential and simultaneous administration.

"Feed supplement" refers to a supplement for administration to an animal that provides a benefit, such as by way of example and without limitation, a nutrient and/or health benefit. The feed supplement may be a non-medicated supplement. Benefits may include, but are not limited to, improving a nutrient balance, enhancing the animal's immune system, providing a nutrient substantially missing from the feed, improving feed conversion, and/or reducing deleterious effects, such as stress effects and/or side effects, of administration of a medicament.

"Micro tracers" refers to an additive that can be used for a variety of purposes, such as a processing aid to carry out various analyses, such as tracing products sold, spillage or carry over, and/or to assess mixing, storage and transport processes. Exemplary disclosed micro tracers comprise iron particles coated with a colorant or dye, such as a food colorant.

"Effective amount" refers to an amount of a compound or composition sufficient to provide a benefit to a subject, such as an animal, such as to treat a specified disorder or disease, to ameliorate or eradicate one or more of its symptoms and/or to prevent the occurrence of the disease or disorder. A person of ordinary skill in the art will understand that the amount of a compound constituting an "effective amount" will vary depending on the nature of the subject to which it is administered, the compound or composition, the disease state and its severity, the age of the subject to be treated, and the like.

"Wheat middlings" or "wheat midds" refers to a waste product of wheat milling. Wheat middlings typically comprise, consist essentially of, or consist of, fine particles of wheat bran, wheat shorts, wheat germ, wheat flour, and other material that is left over after an initial milling process is complete. Wheat middlings may be obtained from commercial milling, and may comprise 9.5% or less crude fiber.

"Therapeutic agent" refers to an agent that has a therapeutic and/or beneficial effect when administered to a subject, such as an animal. For particular disclosed embodiments, "therapeutic agents" are those that may be formulated into a composition comprising wheat middlings, with nicarbazin being one example of a suitable therapeutic agent.

II. Composition

Embodiments of the disclosed composition comprise a therapeutic agent and a carrier particularly selected to have, or a carrier processed to have, a desired composite flow index (CFI). In some embodiments, the carrier is selected to produce a composition having a CFI of greater than 40 to 100, such as from greater than 40 to 70, from 50 to 60, more typically, from 55 to 60. The carrier may be selected to produce a composition having an angle of repose of greater than zero to 40, such as from 10 to 40, from 20 to 40 or from 30 to 40; a percent compressibility of from zero to 20%, such as from greater than zero to 20%, or from 10% to 20%; and/or a critical orifice diameter of from greater than zero to 30, such as from 15 to 30, or from 20 or 30. The desired CFI may be an improved CFI, compared to a CFI of a different and/or non-processed carrier. For certain disclosed embodiments, the carrier may be wheat middlings, such that the composition comprises a therapeutic agent and wheat middlings processed to have an improved CFI relative to non-processed wheat middlings. Certain disclosed processed wheat middlings are sorted to have a size of from 20 mesh to 80 mesh. Optionally, the composition may further comprise an oil, one or more micro tracers, and/or any other component commonly added to such compositions for administration.

The therapeutic agent may be any therapeutic agent now known or hereafter developed that is suitable for administration to a subject, particularly an animal, that may be formulated with a carrier processed to have an improved CFI, such as wheat middlings processed to have an improved CFI. Exemplary therapeutic agents include, but are not limited to, amprolium; avilamycin; bacitracin methylene disalicylate (bmd); zinc bacitracin; bambermycin; carbadox; ceftiofur; chlortetracycline; clopidol; decoquinate; diclazuril; dihydrostreptomycin; enrofloxacin; erythromycin; fenbendazole; flavomycin; florfenicol; gentamicin; sulphadimidine; ivermectin; laidlomycin; lasalocid; lincomycin; maxiban; meduramicin ammonium; monensin; morantel tartrate; narasin; neomcyin sulfate; nicarbazin; niclosamide; oxytetracycline; penicillin, such as procaine penicillin, benzathine penicillin, ampicillin, penicillin G, penicillin V and/or amoxicillin; poloxalene; pyrantel tartrate; ractopamine; robenidine; roxarsone; salinomycin; semduramicin; spectinomycin; stenorol; sulphadimidine; sulfadimethoxine; terramycin; neo-terramycin; tetracycline; tiamulin; tilmicosin; thiabendazole; toltrazuril; trimethoprim; tulathromycin; tylosin; virginiamycin; zoalene; or any combination thereof. In certain embodiments, the therapeutic agent is nicarbazin.

The oil may be any oil suitable for administration to a subject, such as an animal. In certain embodiments, the oil is soybean oil, mineral oil, or a combination thereof.

The carrier may be any carrier suitable for use with a particular therapeutic agent or combination of therapeutic agents, and having, or processed to have, a desired CFI. In some embodiments, the carrier is selected to provide a desired CFI in a particular composition, such as an improved composition CFI, compared to a CFI of a composition comprising a different and/or non-processed carrier. With particular reference to wheat middlings as a carrier, the wheat middlings may be granular wheat middlings, and/or wheat middlings that are not flaky or powdery particles. The wheat middlings used in certain disclosed embodiments are compressed into pellets and then processed, such as by using a roller mill, to form granules and/or non-flaky and non-powdery particles.

In some embodiments, the wheat middlings are particles, such as granular or non-flaky and non-powdery particles, having a size range of from 0.18 mm (80 mesh) to 1 mm (18 mesh), such as, from 0.18 mm (80 mesh) to 0.84 mm (20 mesh). In some embodiments, at least 40% by weight of the wheat middling particles in the composition, such as at least 50%, at least 60%, at least 70%, at least 80%, at least 85%, at least 90%, at least 95%, or at least 97% of the particles, are granules having a particle size of from 0.18 mm (80 mesh) or greater to 1 mm (18 mesh), such as from 0.18 mm (80 mesh) or greater to 0.84 mm (20 mesh).

In some embodiments, the composition comprises from greater than zero to 50 wt % or more of the therapeutic agent, and from 40 wt % or less to 90 wt % or more of a carrier, such as wheat middlings, such as from 10 wt % to 40 wt % therapeutic agent to 60 wt % to 90 wt % wheat middlings. The composition may comprise from 1 wt % to 10 wt % or more oil, from 10 wt % to 50 wt % therapeutic agent, from greater than zero to 1 wt % micro tracers (if present), and from 40 wt % to 90 wt % of a carrier, such as wheat middlings.

In particular embodiments, the composition comprises, consists essentially of, or consists of, wheat middlings, nicarbazin, soybean oil and optionally micro tracers. In some embodiments, the relative amounts of the composition are from 2 wt % to 4 wt % soybean oil, from 10 wt % to 30 wt % nicarbazin, from greater than zero to 1 wt % micro tracers (if present), and from 65 wt % to 88 wt % wheat middlings, such as 2 wt % to 4 wt % soybean oil, from 22 wt % to 28 wt % nicarbazin, from greater than zero to 1 wt % micro tracers, and from 67 wt % to 76 wt % wheat middlings, or from 2.5 wt % to 3.5 wt % soybean oil, from 23 wt % to 27 wt % nicarbazin, from 0.2 wt % to 0.7 wt % micro tracers, and from 68.8 wt % to 74.3 wt % wheat middlings. In certain working embodiments, the composition consists of 3 wt % soybean oil, 25 wt % nicarbazin, 0.5 wt % micro tracers, with the remaining 71.5 wt % being wheat middlings.

In certain working embodiments, the composition comprises, consists essentially of, or consists of, 3% soybean oil, 25% nicarbazin, 0.5% micro tracers, and 71.% processed granular wheat middlings particles where at least 90%, such as 95% or 97%, of the particles have a size range of from 0.18 mm (80 mesh) to 0.84 mm (20 mesh).

Disclosed embodiments of processed carriers, compositions comprising processed carriers, or both, may be described with reference to a CFI. In some embodiments, appropriate processed carriers, such as granular wheat middlings, may have an angle of repose of greater than zero to 40, a percent compressibility of from zero to 20%, a critical orifice diameter of from greater than zero to 15, and/or a CFI of greater than 45 to 100.

With reference to certain disclosed compositions, such compositions may have a CFI of from greater than 45 to 100, such as from 50 to 100, from 55 to 100 or from 58 to 100.

The CFI is calculated by first determining the angle of repose in degrees, the critical orifice index (in mm) and the percentage compressibility. FIG. 1 is a schematic diagram illustrating how the angle of repose can be determined. With respect to FIG. 1, a composition stream 100 is allowed to flow onto a level surface 102 such that it forms a cone 104. The angle of repose is the angle 106 described by the side of the cone 104 and the surface 102.

The critical orifice index can be determined by using a container, such as a cylinder, with a variable opening at the bottom. A component of a composition or the composition is placed in the container and the critical orifice index is the diameter of the smallest opening through which the composition will flow.

The percentage compressibility can be determined by placing a known weight of the composition in a graduated container, such as a graduated cylinder, and determining the volume before and after tapping to pack the particles. The density of the material before and after tapping can be determined as follows:

Bulk density=weight of composition/volume before tapping

Tapped density=weight of composition/tapped volume.

The percentage compressibility is then calculated as:

% compressibility=[1−bulk density/tapped density]× 100.

Then a composite index of each of the three parameters is determined:

Composite critical orifice index=−1 1/9×point value+ 37 7/9;

Composite index of compressibility=−2/3×% compressibility+36 2/3;

Composite index of the angle of repose=−2/3×angle of repose+50.

The CFI is calculated as the sum of the composite indices:

CFI=Composite critical orifice index+Composite index of compressibility+Composite index of the angle of repose.

Additional information concerning calculating the CFI can be found in Taylor et al. Composite Method to Quantify Powder Flow as a Screening Method in early Tablet or Capsule Formulation Development, *AAPS Pharm Sci Tech*, 2000, vol. 1(3), article 18, which is incorporated herein by reference in its entirety.

Table 1 provides raw data and the CFI for an exemplary embodiment of granular wheat middlings having a size range of from 20 to 80 mesh, three exemplary embodiments of the disclosed composition, a commercial embodiment of a nicarbazin composition comprising non-granular wheat middlings, i.e. wheat middlings that have not been compression processed into pellets and then crushed to form granules, and an exemplary sample of the non-granular wheat middlings having a size range of from 30 to 80 mesh.

TABLE 1

Raw data and composite flow index

| No. | Sample | Raw Data | | | Composite Flow Index |
|---|---|---|---|---|---|
| | | Angle of Repose | % Compressibility | Critical Orifice Diameter | |
| 1 | Granular wheat middlings 20-80 | 37.57 | 17.98 | 7 | 79.6 |
| 2 | Exemplary embodiment 1 | 34.70 | 17.65 | 28 | 58.4 |
| 3 | Exemplary embodiment 2 | 37.57 | 12.63 | 28 | 59.9 |
| 4 | Exemplary embodiment 3 | 36.14 | 11.58 | 30 | 59.3 |
| 5 | Commercial sample | 50.91 | 23.68 | 34 | 36.9 |
| 6 | Non-granular wheat middlings 30-80 | 48.30 | 23.73 | 32 | 40.8 |

In some embodiments, compositions comprising carriers, such as processed granular wheat middlings, have a CFI at least 30% greater that the CFI of corresponding compositions that do not comprise granular wheat middlings, but instead comprise non-processed, non-granular, such as powdered and/or flaky, wheat middlings. Compositions comprising the granular wheat middlings may have a CFI of from 30% to 200% or more greater than corresponding compositions with non-granular wheat middlings, such as from 35% to 200%, from 40% to 200%, from 45% to 170%, from 50% to 170%, from 55% to 150% or from 60% to 150% greater than corresponding compositions with non-granular wheat middlings.

In some embodiments, appropriate carriers, such as processed carriers, particularly granular wheat middlings, may have an angle of repose of greater than zero to 40, such as from 10 to 40, from 20 to 40, from 30 to 40, or from 35 to 40. In some embodiments, appropriate carriers, such as granular wheat middlings, have a percent compressibility of from zero to 20%, such as from greater than zero to 20%, from 10% to 20%, or from 15% to 20%. Appropriate carriers, such as granular wheat middlings, may have a critical orifice diameter of from greater than zero to 15, such as from 1 to 10, from 3 or 10, or from 3 to 8. And certain examples of appropriate carriers, such as granular wheat middlings, have a CFI of greater than 45 to 100, such as from 50 to 90, from 60 to 85, or from 70 to 85. In some embodiments, the appropriate carrier may have a CFI of at least 50% greater than the CFI of the corresponding carrier that has not been processed to have an improved CFI, such as by granulation. The appropriate carrier may have a CFI of from 50% to 200% or more greater than the corresponding non-granular carrier, such as from 60% to 200%, from 70% to 200%, from 75% to 200%, from 80% to 180%, from 85% to 175%, from 90% to 150%, or from 95% to 125% greater than the corresponding non-granular carrier.

Additionally, certain embodiments of the disclosed compositions have an angle of repose of greater than zero to 40, such as from 10 to 40, from 20 to 40 or from 30 to 40. In some embodiments, the composition has a percent compressibility of from zero to 20%, such as from greater than zero to 20%, or from 10% to 20%. Embodiments of the composition may have a critical orifice diameter of from greater than zero to 30, such as from 15 to 30, or from 20 or 30. And certain embodiments of the disclosed composition have a CFI of greater than 40 to 100, such as from greater than 40 to 70, from 50 to 60, more typically, from 55 to 60. Table 2 provides a correlation between flow characteristics or description and CFI.

TABLE 2

CFI and Flow Description

| Flow Description | CFI |
|---|---|
| Excellent | >85 |
| Good | >75-85 |
| Fair | >60-75 |
| Passable | >45-60 |
| Poor | >30-45 |
| Very Poor | >15-30 |
| Very, Very Poor | ≤15 |

Tables 1 and 2 clearly show a benefit correlated to CFI when granular wheat middlings are used to make disclosed compositions compared to, for example, a commercial nicarbazin composition that does not include granular wheat middlings. For example, known commercial nicarbazin formulations samples have a CFI of 36.9, i.e. a composition exhibiting poor flow characteristics. Conversely, compositions comprising granular wheat middlings have CFI values at least 20 points higher than the commercial product, indicating that they have significantly improved flow characteristics.

In some embodiments, the disclosed composition may be combined with a feed to form a mixed composition. The feed may be any feed suitable for feeding to an animal, including, but not limited to, a poultry feed, bovine feed, swine feed, equine feed, sheep feed, or goat feed. In certain embodiments, the feed is a poultry feed. The feed may comprise corn; soybean meal; soybean oil; wheat; barley; rye; rice hulls; canola; corn oil; limestone; salt (for example; sodium chloride); distillers dried grains with solubles (DDGS); phosphates, such as dicalcium phosphate; sesquicarbonates, such as sodium sesquicarbonate; methionine source; lysine source; L-threonine; mineral oil; biotin; folic acid; kelp; menadione dimethylpyrimidinol bisulfite; calcium aluminosilicate; or any combination thereof. The feed may also comprise one or more additional components. Additional components may be used for any desired purpose, such as a substantially biologically inert material added, for example, as a filler, or to provide a desired beneficial effect. For example, the feed may include a carbonate (including a metal carbonate such as calcium carbonate); a trace mineral, such as, but not limited to, chloride, fluoride, iodide, chromium, copper, zinc, iron, magnesium, manganese, molybdenum, phosphorus, potassium, sodium, sulfur, selenium, or a combination thereof; a bulking agent; a carrier; a colorant; a taste enhancer; a preservative; one or more vitamins; or a combination thereof. The preservative may be benzoic acid or a salt thereof, e.g. sodium benzoate; lactic acid or a salt thereof, e.g. sodium lactate, potassium lactate or calcium lactate; propionic acid or a salt thereof, e.g. sodium propionate; ascorbic acid or a salt thereof, e.g. sodium ascorbate; gallic acid or a salt thereof e.g. sodium gallate; sulfur dioxide and/or sulfites; nitrites; nitrates; choline, or a salt thereof, such as an anion salt of choline, e.g. choline halide, such as chloride, bromide, iodide, fluoride, or choline hydroxide; or any combination thereof. The one or more vitamins may include vitamin A; vitamin $B_1$, such as thiamine mononitrate; vitamin $B_2$, such as riboflavin-5-phosphate; vitamin $B_3$, such as niacin or niacinamide; vitamin $B_5$, such as pantothenic acid or d-calcium pantothenate; vitamin $B_6$, such as pyridoxine or pyridoxine hydrochloride; vitamin $B_{12}$; vitamin C, such as ascorbic acid, sodium ascorbate, or calcium sorbate; vitamin D; vitamin E; vitamin K; or a combination thereof. Vitamin D may comprise vitamin $D_1$, vitamin $D_2$, vitamin $D_3$, vitamin $D_4$, vitamin $D_5$, 25-hydroxy vitamin $D_3$, 25-dihydroxy vitamin $D_3$, or combinations thereof.

III. Method for Making Composition Embodiments

A general method for making the disclosed composition comprises selecting a carrier, or processing a carrier, to have desired properties, particular a suitable CFI, such as processed granular wheat middlings and making desired compositions by combining the carrier with at least a therapeutic agent. With particular reference to providing suitable granular wheat middlings, the processing method may comprise pelletizing powdered and/or flakey wheat middlings to form pellets. The pellets are then milled to form the granular wheat middlings. The method may further comprise sorting, such as by sieving, the granular wheat middlings to form granular wheat middlings having a desired size range, such as 18-80 mesh or 20-80 mesh, or about 0.18 mm to 0.84 mm.

Figure 2:
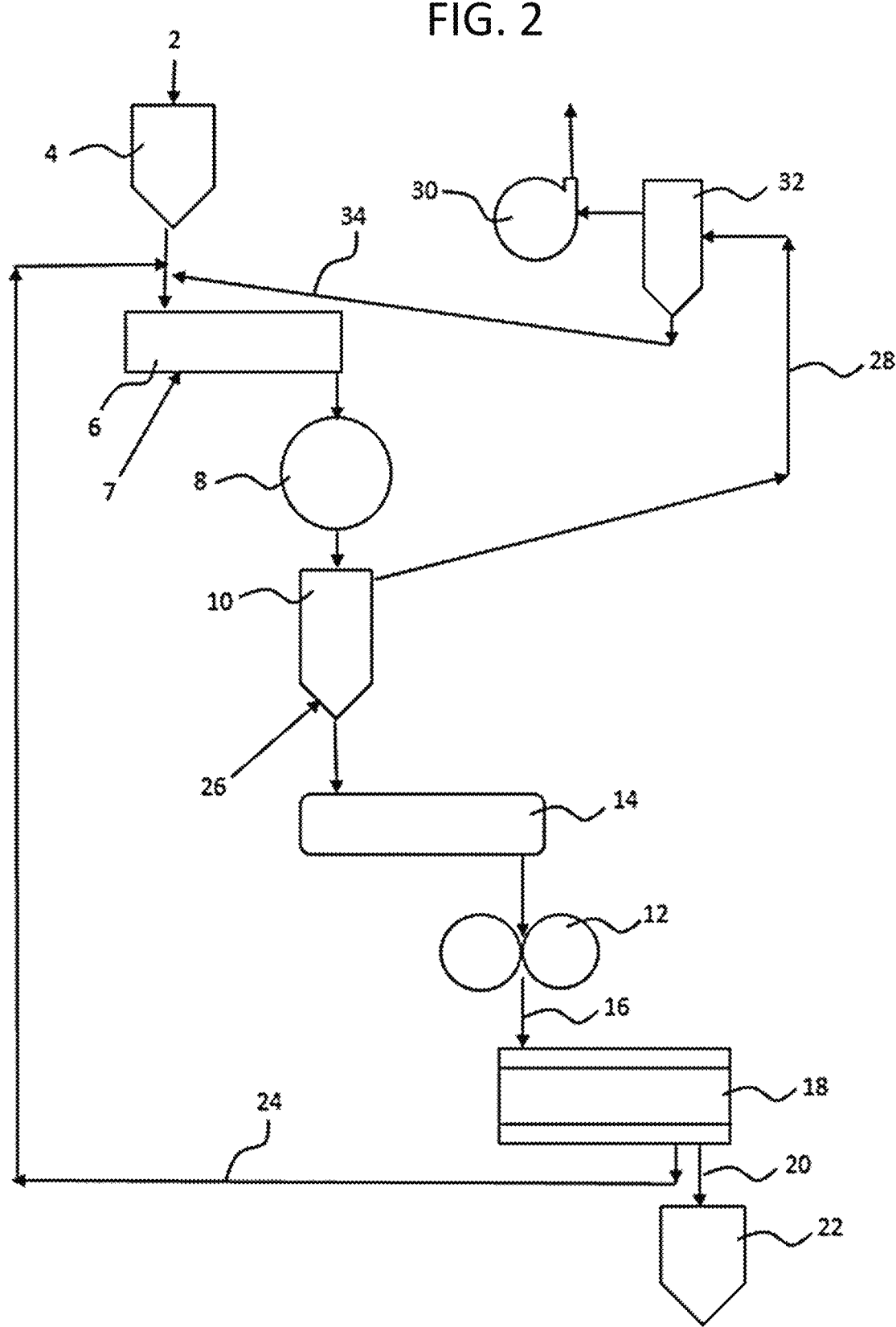
FIG. 2 is a schematic flow diagram illustrating an exemplary embodiment of a method and system for preparing granular wheat middlings.

FIG. 2 provides a schematic diagram illustrating an exemplary embodiment of a system and method to prepare granular wheat middlings. With reference to FIG. 2, wheat middlings 2, typically powdered and/or flakey wheat middlings, are placed in a suitable container 4, such as a silo or hopper. The wheat middlings 2 pass through a conditioner 6 where they are heat-treated, such as by exposure to a steam stream 7. After the conditioner 6, the wheat middlings 2 are processed in a pellet mill 8, where they are formed into pellets. The pellets may be produced in a die plate (not shown), having a hole diameter of from greater than zero to ½ inch or more, such as from greater than zero to ¼ inch, or from 5/64 inch to ¼ inch, and/or a die plate thickness of from greater than zero to 3 inches or more, such as from 1 inch to 3 inches, or from 1½ inches to 2½ inches. In some embodiments, the die plate has a hole diameter of about 11/64 inch and/or a die plate thickness of about 2 inches. The pellets may be cooled, such as to ambient temperature, in a cooler 10 before being milled by a suitable mill 12, such as a roller mill. The cooling process may comprise passing a stream of air over the pellets (not shown). The pellets may be moved from the cooler 10 to the mill 12 by any suitable technique, such as a conveyer 14. The mill 12 may be any mill suitable to mill the pellets into milled wheat middlings particles or granules, i.e. particles that are substantially not powdered or flakey. In some embodiments, mill 12 comprises a roller mill, and may comprise a three stage roller mill. The milled wheat middlings 16 are then sorted into a desired size range by a screener 18, such as a multiple deck screener, to separate the granular wheat middlings 20 having the desired size range from oversized and/or undersized particles. The screener 18 may comprise any suitable size sorting techniques, such as, but not limited to, screens or sieves. Typically, the granular wheat middlings 20 within the desired size range are stored in a suitable container 22, such as a silo or hopper, ready for use in a nicarbazin formulation blending process. Oversized and undersized particles 24 may be recycled and reintroduced into the process prior to pelletization in the pellet mill 8.

Optionally, an air stream 26 may be introduced into the cooler 10. Air stream 28 exits the cooler 10 and may comprise some dust particles. A blower 30 may be used to pull air stream 28 through cooler 10 and through a separator 32 that separates the blown dust wheat middlings particles from the air. The separator 32 may be any suitable separator, such as a cyclone separator. The separated wheat middlings stream 34 can be combined with wheat middlings 2 at any stage prior to pelletization. In some embodiments, the separated wheat middlings stream 34 is combined with wheat middlings 2 prior to, or in, the conditioner 6.

Figure 3:
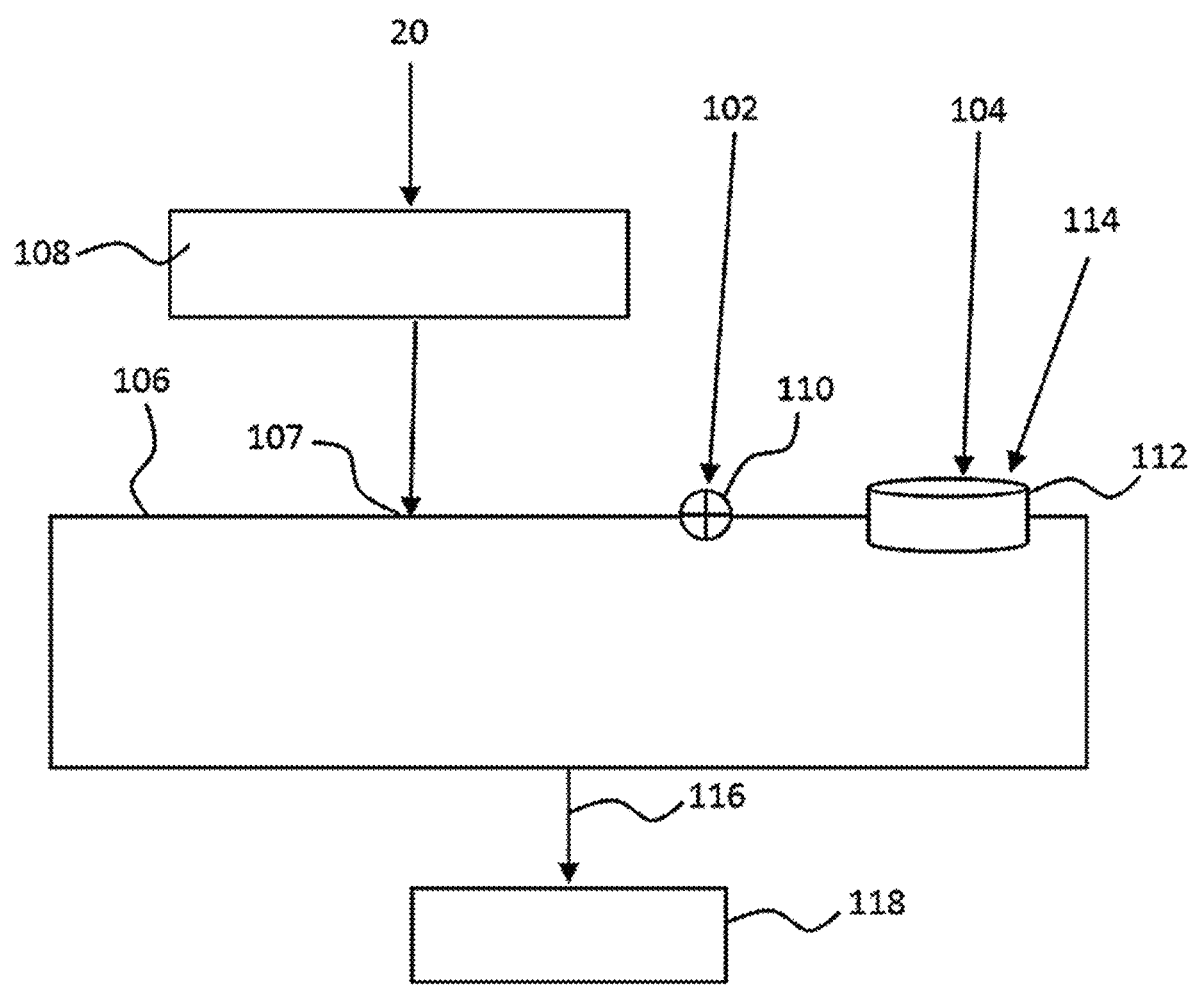
FIG. 3 is a schematic flow diagram illustrating an exemplary embodiment of a method for preparing a composition comprising a therapeutic and granular wheat middlings.

The blending process to make disclosed composition embodiments may comprise forming a mixture comprising, consisting essentially of, or consisting of, an appropriately selected or processed carrier, such as processed granular wheat middlings 20 and a therapeutic agent, such as nicarbazin, and optionally an oil, such as soybean oil or mineral oil, and/or micro tracers. FIG. 3 is a schematic diagram that describes one exemplary embodiment of the blending process. With reference to FIG. 3, a desired amount of an appropriate carrier, such as processed granular wheat middlings 20 having a suitable size range, are combined with a desired amount of oil 102 and therapeutic agent 104 and in a suitable mixer 106 to form a mixture. Mixer 106 may be any mixer suitable to mix the components to form a mixture. In some embodiments, the mixer is a centrifugal and/or rotary mixer. In some embodiments, an appropriate carrier, such as processed wheat middlings 20, may be introduced to the mixer through a wheat middlings inlet 107, and optionally are weighed by a scale 108 prior to being added to the mixer 106. Oil 102 may be added to mixer 106 through an oil inlet 110, by any suitable technique, such as spraying, pouring, dropwise or portionwise addition, or adding as a stream. In certain embodiments, oil 102 is added as a spray, such as by a pump-spray system. Therapeutic agent 104 may be added to mixer 106 through a therapeutic agent inlet 112 that may comprise a screener. The screener screens out lumps or particles in the therapeutic agent and any large contaminant particles that may be present.

An appropriate carrier, such as processed wheat middlings 20, oil 102 and therapeutic agent 104 may be added to the mixer 106 substantially simultaneously or sequentially in any order. In some embodiments, the wheat middlings are added to the mixer 106 before oil 102 and/or therapeutic agent 104. In certain embodiments, the wheat middlings 20 are added followed by oil 102, and then therapeutic agent 104.

Optionally wheat middlings 20 and oil 102 are mixed prior to therapeutic 104 being added. Without being bound to a particular theory, combining the wheat middlings and oil prior to the addition of therapeutic agent 104, optionally by spraying the oil onto the wheat middlings, and/or by mixing, such as stirring, during addition of the wheat middlings and oil, may allow the oil to intimately mix with the wheat middlings, i.e. be substantially evenly distributed throughout the wheat middlings. The oil may substantially coat the wheat middling granules. Optionally, after combining, the wheat middlings/oil mixture may be mixed, such as by stirring, for a first period of time suitable to produce the intimate mixture of the wheat middlings and oil. The first period of time may be from greater than zero to 10 minutes or more, such as from 1 minute to 7 minutes, or from 3 minutes to 5 minutes. Substantially evenly distributing the oil throughout the wheat middlings may help facilitate therapeutic agent 104 binding or sticking to the granular wheat middlings 20 and/or being evenly distributed throughout the mixture. In this manner, a product is formed comprising a therapeutic agent, such as nicarbazin, coated, or at least partially coated, with a carrier having a selected, or processed to have a selected, CFI.

Optionally, micro tracers 114 may be added to the mixture. Micro tracers 114 may be added at any time during the mixing process, such as with therapeutic agent 104, or after the therapeutic agent is added. The micro tracers may be added through the therapeutic agent inlet 112, as illustrated in FIG. 3, or they may be added via a separate micro tracer inlet (not shown).

Mixer 106 may continuously mix the components during their addition, or the mixer may intermittently stop actively mixing, such as for example, during time periods when components are being added. In some embodiments, the mixture is mixed for a period of time after the last component has been added, to facilitate forming a substantially uniform mixture, that is, a substantially homogenous blend of the components. In some embodiments, the time period is as short as possible to form a uniform mixture while minimizing possible attrition of the granular wheat middlings. Typically, the time period is from greater than zero to 30 minutes or more, such as from 5 minutes to 25 minutes, or from 10 minutes to 20 minutes.

After mixing, the mixture 116 is conveyed to a packaging location 118 by a suitable technique, such as a conveyor belt and/or gravity, where the mixture is packaged into appropriate packaging for transport, sale, and/or use.

IV. Method of Using the Composition

A. Animals

Embodiments of the disclosed composition are administered to an animal, such as a human or non-human animal. The animal may be a land animal, an aquatic animal, an avian, or an amphibian. The animal may be a mammal, or a non-mammal. The non-human animal can be an animal raised for human consumption or a domesticated animal. Examples of animals that can be fed and/or administered the disclosed composition include, but are not limited to, ruminant species, such as a sheep, goat, cow, deer, bison, buffalo, elk, alpaca, camel or llama; ungulates, such as a horse, donkey, or pig; avians, such as chickens, including laying hens and broilers, turkey, goose, duck, Cornish game hen, quail, partridge, pheasant, guinea-fowl, ostrich, emu, swan; or pigeon, aquatic animals, such as an aquaculture species, such as fish (e.g., salmon, trout, tilapia, sea bream, carp, cod, halibut, snapper, herring, catfish, flounder, hake, smelt, anchovy, lingcod, moi, perch, orange roughy, bass, tuna, mahi mahi, mackerel, eel, barracuda, marlin, Atlantic ocean perch, Nile perch, Arctic char, haddock, hoki, Alaskan Pollock, turbot, freshwater drum, walleye, skate, sturgeon, Dover sole, common sole, wolfish, sablefish, American shad, John Dory, grouper, monkfish, pompano, lake whitefish, tilefish, wahoo, cusk, bowfin, kingklip, opah, mako shark, swordfish, cobia, croaker, or hybrids thereof, and the like); crustaceans (e.g., lobster, shrimp, prawns, crab, krill, crayfish, barnacles, copepods, and the like); or molluscs (e.g., squid, octopus, abalone, conchs, rock snails, whelk, clams, oysters, mussels, cockles, and the like).

B. Uses of the Composition

The composition may be used to treat and/or prevent an infection in an animal. The infection may be a bacterial, parasitic, or viral infection. In some embodiments, the infection is a parasitic infection, including, but not limited to, coccidiosis or kudoa. Coccidiosis is a parasitic disease of the intestinal tract of animals caused by coccidian protozoa of the genus *Eimeria*. The disease can spread amongst animals by contact with infected feces by means of an infective form called the oocyst. Coccidiosis is a significant disease of certain animals, such as domestic fowl and livestock, as it can affect animals at a very young age. It can be fatal or compromise animal health, thereby impairing the feed conversion rate of the animals. Thus, production, reproductive efficiency and animal health are adversely affected by coccidiosis. Diseases, such as coccidiosis, cause significant economic losses in certain animal industries. Such diseases also can negatively affect the health of domesticated animals.

Kudoa infections are caused by a myxozoan parasite of the genus Kudoa. Kudoa infections can occur in a wide variety of aquatic animals, such as fish, particularly marine fish. Kudoa infections occur worldwide. Kudoa species that can cause Kudoa infections include, but are not limited to Kudoa alliaria, Kudoa anamiensis, Kudoa azevedoi, Kudoa azoni, Kudoa camarguensis, Kudoa cascasia, Kudoa caudata, Kudoa chaetodoni, Kudoa cheilodipteri, Kudoa chilkaensis, Kudoa ciliatae, Kudoa clupeidae, Kudoa cookii, Kudoa crumena, Kudoa cynoglossi, Kudoa dianae, Kudoa funduli, Kudoa graminatorcyni, Kudoa gunterae, Kudoa histolytica, Kudoa hypoepicardialis, Kudoa inornata, Kudoa insolita, Kudoa intestinalis, Kudoa iwatai, Kudoa kabatai, Kudoa kenti, Kudoa lateolabracis, Kudoa leiostomi, Kudoa lethrini, Kudoa lunata, Kudoa lutjanus, Kudoa megacapsula, Kudoa miniauriculata, Kudoa minithyrsites, Kudoa mirabilis, Kudoa monodactyli, Kudoa musculoliquefaciens, Kudoa nova, Kudoa ovivora, Kudoa paniformis, Kudoa paralichtys, Kudoa paraquadricornis, Kudoa pericardialis, Kudoa permulticapsula, Kudoa quadratum, Kudoa quadricornis, Kudoa rosenbuschi, Kudoa sciaenae, Kudoa scomberomori, Kudoa sebastea, Kudoa shkae, Kudoa sphyraeni, Kudoa stellula, Kudoa tachysurae, Kudoa tetraspora, Kudoa thalassomi, Kudoa thyrsites, Kudoa whippsi, or a combination thereof. In certain embodiments, the Kudoa infection is a Kudoa thyrsites infection. The parasite causes a post-mortem degradation or softening of the fish's muscle tissue that affects the texture and commercial value of the fish. Kudoa infections, such as infections by *K. thyrsites*, are a particular problem for open water net pens, where the fish are exposed to untreated sea water. In aquaculture, *K. thyrsites* infections are a significant problem, particularly in the farming of salmon, such as Atlantic salmon.

It will be understood by a person of ordinary skill in the art (e.g., a veterinarian) that the amount of the disclosed composition that is administered to an animal can be a therapeutically effective amount for a particular animal species. In some embodiments, the amount of the disclosed composition used can range from greater than 0 ppm to 100,000 ppm, such as 0.25 ppm to 5,000 ppm, or 0.5 ppm to 2,500 ppm, or 0.75 ppm to 2,000 ppm, or 1 ppm to 1,500 ppm, or 5 ppm to 1,000 ppm, or 10 ppm to 500 ppm, or 25 ppm to 300 ppm. In other embodiments, the amount of the disclosed composition used can range from greater than 0 mg/kg of body weight to 100,000 mg/kg of body weight, such as 0.5 mg/kg to 2,500 mg/kg, or 1 mg/kg to 1,500 mg/kg, or 5 mg/kg to 1,000 mg/kg, or 10 mg/kg to 500 mg/kg m, or 25 mg/kg to 300 mg/kg, or 10-20 mg/kg.

In some embodiments, the amount of the disclosed composition that is mixed with a feed can range from at least 1 g/ton of feed to 250 g/ton of feed (or at least 1 ppm to 275 ppm), such as at least 1 g/ton of feed to 200 g/ton of feed (or at least 1 ppm to 242 ppm), or at least 1 g/ton of feed to 150 g/ton of feed (or at least 1 ppm to 165 ppm), and in certain embodiments, the amount of the disclosed composition that is mixed with feed is sufficient to provide from 60 g nicarbazin/ton of feed to 113 g nicarbazin/ton of feed (or 66 ppm to 125 ppm).

C. Combinations with Other Therapeutic Agents and Vaccines

The disclosed composition can also be used in combination with other therapeutic agents including, by way of example and without limitation, antimicrobials including antibiotics and/or anticoccidial agents, and vaccines. Exemplary other antimicrobials include, but are not limited to, amprolium; avilamycin; bacitracin methylene disalicylate (bmd); zinc bacitracin; bambermycin; carbadox; ceftiofur; chlortetracycline; clopidol; decoquinate; diclazuril; dihydrostreptomycin; enrofloxacin; erythromycin; fenbendazole; flavomycin; florfenicol; gentamicin; sulphadimidine; ivermectin; laidlomycin; lasalocid; lincomycin; maxiban; meduramicin ammonium; monensin; morantel tartrate; narasin; neomcyin sulfate; nicarbazin; niclosamide; oxytetracycline; penicillin, such as procaine penicillin, benzathine penicillin, ampicillin, penicillin G, penicillin V and/or amoxicillin; poloxalene; pyrantel tartrate; ractopamine; robenidine; roxarsone; salinomycin; semduramicin; spectinomycin; stenorol; sulphadimidine; sulfadimethoxine; terramycin; neo-terramycin; tetracycline; tiamulin; tilmicosin; thiabendazole; toltrazuril; trimethoprim; tulathromycin; tylosin; virginamycin; zoalene; or any combination thereof.

Suitable vaccines can be selected from live coccidiosis vaccines, such as COCCIVAC (e.g., a composition comprising live oocysts of *Eimeria acervulina, Eimeria mivati, Eimeria maxima, Eimeria mitis, Eimeria tenella, Eimeria necatrix, Eimeria praecox, Eimeria brunetti, Eimeria hagani*, or combinations thereof); LivaCox (a composition comprising 300-500 live sporulated oocysts of each attenuated line of *Eimeria acervulina, E. maxima* and *E. tenella* in a 1% w/v aqueous solution of Chloramine B); ParaCox (a composition comprising live sporulated oocysts derived from *E. acervulina* HP, *E. brunetti* HP, *E. maxima* CP, *E. maxima* MFP, *E mitis* HP, *E. necatrix* HP, E. *praecox* HP, *E. tenella* HP, and combinations thereof); Hatch Pack Cocci III (a composition comprising oocysts derived from *Eimeria acervulina, Eimeria maxima, Eimeria tenella*, or combinations thereof); INOVOCOX (a composition comprising oocysts derived from *Eimeria acervulina, Eimeria maxima, Eimeria tenella*, and a sodium chloride solution); IMMU-COX (a composition comprising live oocysts derived from *Eimeria acervulina, Eimeria maxima, Eimeria necatrix, Eimeria tenella*, and combinations thereof); Advent; or combinations thereof.

In yet additional embodiments, other vaccines can be utilized. For example, any vaccine suitable for use in any of the animals described herein can be used in the disclosed combinations and methods. In some embodiments, the vaccine can be selected based on the particular animal to receive the combination. In some embodiments, the vaccine can be selected based on the particular diseases to which a particular animal is susceptible. Solely by way of example, a vaccine administered to a ruminant can be selected from any vaccine suitable for preventing or treating sudden death (e.g., clostridial diseases, anthrax, and the like), respiratory diseases (e.g., infectious bovine rhinotracheitis, parainfluenza-3, bovine virus diarrhea, bovine respiratory syncytial virus, pasteurella, haemophilus sommus, and the like), reproductive diseases (IBR, BVD, brucellosis, vibriosis, lepto, trichomoniasis, and the like), scours (rota and corona virus, *E. coli*, and the like), pinkeye, hepatitis E virus, porcine endogenous retrovirus, swine influenza virus, porcine parvovirus, and the like. In some embodiments, vaccines can be selected from B ALPHA, BAR-GUARD-99, BAR-VAC, BIOMYCIN 200, BO-BAC-2X, BOVIKALC, CALIBER, CITADEL, CYDECTIN INJECTABLE, CYDECTIN POUR-ON, C & D ANTITOXIN, DIAQUE, DRY-CLOX, ENTERVENE-D, EXPRESS, EXPRESS FP, HETACIN-K, LYSIGIN, OCU-GUARD MB-1, POLY-FLEX, PRESPONSE, PRISM 5, PYRAMID, PYRAMID, PRESPONSE SQ, QUATRACON-2X, SYNANTHIC, TODAY, TOMORROW, TRIANGLE, TRIVIB 5L, TRICH-GUARD, and the like. In yet additional embodiments, the vaccine can be selected from CIRCUMVENT PCV G2, CIRCUMVENT PCV-M G2, MAGESTIC 7, MAXIVAC, EXCELL 5.0, PROSYSTEM RCE, PROSYSTEM ROTA, TGE/ROTA, PROSYSTEM TREC, and the like.

Additional suitable vaccines include vaccines for Marek's disease, such as MD-Vac, HVT, SB-1, Rispens CVI 988, VAXXITEK (HVT+IBD); vaccines for Newcastle disease, such as CLONEVAC-30, Newcastle-Bronchitis Poultry Vaccine, Clone 30, Hitchner B1, TRIPLEVAC, and Newcastle Disease Vaccine; vaccines for infectious bursal disease (IBD), such as VAXXITEK, BUR-CELL, BURSA-BLEN, IBD-BLEN, or Bursa Guard Reo; vaccines for infectious bronchitis, such as TROVAC, H120 vaccine, Ma5 vaccine, IB 4/91 vaccine, or TRIPLEVAC; and vaccines for laryngotracheitis, such as BIO-TRACH or LT-Ivax.

Suitable additional anticoccidial agents include, but are not limited to, ionophores and chemical anticoccidial products. Ionophores can include, but are not limited to, Monensin, Salinomycin, Lasalocid, Narasin, Maduramicin, Semduramicin, Laidlomycin, or combinations thereof. Chemical anticoccidial products can include, but are not limited to, Maxiban, Diclazuril, Toltrazuril, Robenidine, Stenorol, Clopidol, Decoquinate, DOT (zoalene), Amprolium, or combinations thereof. In certain embodiments, the disclosed composition, particularly a nicarbazin composition, is used in combination with Semduramicin.

D. Feed Supplement Comprising *Yucca* and/or *Quillaja*

Additionally, or alternatively, the disclosed composition can be administered in combination with a feed supplement comprising *yucca* and/or *quillaja* plant material. Examples of *yucca* include, but are not limited to, *Yucca aloifolia, Yucca angustissima, Yucca arkansana, Yucca baccata, Yucca baileyi, Yucca brevifolia, Yucca campestris, Yucca capensis, Yucca carnerosana, Yucca cernua, Yucca coahuilensis, Yucca constricta, Yucca decipiens, Yucca declinata, Yucca de-smetiana, Yucca data, Yucca endlichiana, Yucca faxoniana, Yucca filamentosa, Yucca filifera, Yucca flaccida, Yucca gigantean, Yucca glauca, Yucca gloriosa, Yucca grandiflora, Yucca harrimaniae, Yucca intermedia, Yucca jaliscensis, Yucca lacandonica, Yucca linearifolia, Yucca luminosa, Yucca madrensis, Yucca mixtecana, Yucca necopina, Yucca neomexicana, Yucca pallida, Yucca periculosa, Yucca potosina, Yucca queretaroensis, Yucca reverchonii, Yucca rostrata, Yucca rupicola, Yucca schidigera, Yucca schottii, Yucca sterilis, Yucca tenuistyla, Yucca thompsoniana, Yucca treculeana, Yucca utahensis, Yucca valida* or combinations thereof. In certain embodiments, the *Yucca* is or comprises *Yucca schidigera.*

Examples of *quillaja* include, but are not limited to, *Quillaja brasiliensis, Quillaja lanceolata, Quillaja lancifolia, Quillaja molinae, Quillaja petiolaris, Quillaja poeppigii, Quillaja saponaria, Quillaja sellowiana, Quillaja smegmadermos* or combinations thereof. In certain embodiments, the *quillaja* is or comprises *Quillaja saponaria.*

A person of ordinary skill in the art will appreciate that, as used herein, a plant name may refer to the plant as a whole, or to any part of the plant, such as the roots, stem or trunk, bark, leaves, flower, flower stems, or seeds or a combination thereof. These plant parts may be used fresh, or dried, and may be whole, pulverized, or comminuted. The name may also refer to extracts from any part or parts of the plant, such as chemical extracts, or extracts obtained by pressing, or any other methods of concentrating or extracting oils or other extracts known to those in the art or that are hereafter discovered, or the residue remaining after such an extraction. Plant extracts may include compounds that are saponins, triterpenoids, polyphenols, antioxidants or resveratrol, or combinations thereof.

The combination may comprise a feed supplement comprising *yucca* and/or *quillaja* that may also include carriers and binding agents suitable to formulate the *yucca* and/or *quillaja* for administration to an animal. In certain embodiments, such a feed supplement can be a commercially available product, such as a composition comprising *Yucca schidigera* and *Quillaja saponaria*, sold under the trademark NUTRAFITO PLUS by Desert King International and/or MAGNI-PHI by Phibro Animal Health Corporation. Such compositions may comprise 85% *Quillaja saponaria* and 15% *Yucca schidigera* or 90% *Quillaja saponaria* and 10% *Yucca schidigera.*

E. Feed Supplement Comprising Silica, Mineral Clay, Glucan and/or Mannans

Additionally, or alternatively, the disclosed composition can be administered in combination with a feed supplement comprising silica, mineral clay, glucan and mannans. The feed supplement may further comprise an endoglucanohydrolase, either endogenously or as an affirmatively added ingredient. As used herein, weight % for endoglucanohydrolase is based on a 70,000 unit/gram endoglucanohydrolase product. The endoglucanohydrolase may be β-1,3 (4)-endoglucanohydrolase.

In any embodiments disclosed herein, the feed supplement may comprise, consist essentially of, or consist of, glucan (e.g., β-1,3 (4)glucan), silica, mineral clay and mannans. In some embodiments, the feed supplement comprises, consists essentially of, or consists of, glucan (e.g., β-1,3 (4)glucan), silica, mineral clay, mannans and endoglucanohydrolase. In any embodiments disclosed herein, glucans, mannans, endoglucanohydrolase, and any combination thereof, may be provided, at least in part, by yeast cell wall or an extract thereof. Thus, in some embodiments, the feed supplement may comprise, consist essentially of, or consist of, silica, mineral clay and yeast cell wall or an extract thereof, or the feed supplement may comprise, consist essentially of, or consist of, silica, mineral clay, yeast cell wall or an extract thereof, and endoglucanohydrolase.

Suitable sources of silica include, but are not limited to, sand, diatomaceous earth, and synthetic silica. In one embodiment, quartz may be used. In certain embodiments, the mannans comprise glucomannan.

The components of the feed supplement are prepared by methods commonly known in the art and can be obtained from commercial sources. β-1,3 (4)-endoglucanohydrolase may be produced from submerged fermentation of a strain of *Trichoderma longibrachiatum*. Diatomaceous earth is available as a commercially-available product with from 70% to 95% silica ($SiO_2$) and with its remaining components not assayed but primarily ash (minerals) as defined by the Association of Analytical Chemists (AOAC, 2002). The mineral clays (e.g., aluminosilicates) used in this feed supplement may be any of a variety of commercially-available clays including, but not limited to, montmorillonite clay, bentonite and zeolite. Glucan, mannans, and/or endoglucanohydrolase can be obtained from plant cell walls, yeast or yeast cell wall or an extract thereof (e.g., *Saccharomyces cerevisiae, Candida utilis*), certain fungi (e.g., mushrooms), algae, and bacteria. In certain embodiments, yeast can be administered affirmatively to provide glucan, mannans and endoglucanohydrolase endogenously.

In one embodiment, the feed supplement comprises, consists essentially of, or consists of, 1-40 wt % silica, 0.5-25 wt % glucan and mannans, and 40-92 wt % mineral clay, in amounts relative to each other. In another embodiment, the feed supplement comprises, consists essentially of, or consists of, 5-40 wt % silica, 0.5-15 wt % glucan and mannans, and 40-80 wt % mineral clay, in amounts relative to each other. In another embodiment, the feed supplement comprises, consists essentially of, or consists of, 20-40 wt % silica, 0.5 10 wt % glucan and mannans, and 50-70 wt % mineral clay, in amounts relative to each other. In another embodiment, the feed supplement comprises, consists essentially of, or consists of, 15-40 wt % silica, greater than zero to 15 wt % glucans, greater than zero to 10 wt % mannans, and 50-81 wt % mineral clay, in amounts relative to each other. In another embodiment, the feed supplement comprises, consists essentially of, or consists of, 15-40 wt % silica, 0.5-5.0 wt % glucans, 0.5-8.0 wt % mannans, and 50-81 wt % mineral clay, in amounts relative to each other. In another embodiment, the feed supplement comprises, consists essentially of, or consists of, 20-30 wt % silica, 0.5-3.5 wt % glucans, 0.5-6.0 wt % mannans, and 60-70 wt % mineral clay, in amounts relative to each other.

In some embodiments, β-glucans and mannans are obtained from yeast or yeast cell wall or an extract thereof. The feed supplement may comprise, consist essentially of, or consist of, 1-40 wt % silica, 1-30 wt % yeast cell wall or an extract thereof, and 40-92 wt % mineral clay, in amounts relative to each other. In one embodiment, the feed supplement comprises, consists essentially of, or consists of, 10-40 wt % silica, 5-20 wt % yeast cell wall or an extract thereof, and 40-80 wt % mineral clay, in amounts relative to each other. In another embodiment, the feed supplement comprises, consists essentially of, or consists of, 15-30 wt % silica, 5-15 wt % yeast cell wall or an extract thereof, and 50-70 wt % mineral clay, in amounts relative to each other.

In any of the above embodiments, the feed supplement may further comprise an endoglucanohydrolase, such as β-1,3 (4)-endoglucanohydrolase. The feed supplement may include from 0.025 wt % endoglucanohydrolase to 5 wt % endoglucanohydrolase or more, such as from 0.05 wt % to 3 wt % β-1,3 (4)-endoglucanohydrolase, relative to the amounts of silica, mineral clay, glucan, mannans, and/or yeast, yeast cell wall, or yeast cell wall extract present in the feed supplement. In one embodiment, the feed supplement comprises, consists essentially of, or consists of, 0.1 3 wt % β-1,3 (4)-endoglucanohydrolase, 20-40 wt % silica, 0.5-20 wt % glucan and mannans, and 50-70 wt % mineral clay, in amounts relative to each other. In another embodiment, the feed supplement comprises, consists essentially of, or consists of, 0.1-3 wt %, β-1,3 (4)-endoglucanohydrolase, 20-40 wt % silica, 0.5-10 wt % glucan and mannans, and 50-70 wt % mineral clay, in amounts relative to each other. Alternatively, the feed supplement may comprise, consist essentially of, or consist of, 0.1 3 wt % β-1,3 (4)-endoglucanohydrolase, 1-40 wt % silica, 5-30 wt % yeast cell wall or an extract thereof, and 40-92 wt % mineral clay, in amounts relative to each other. In one embodiment, the feed supplement comprises, consists essentially of, or consists of, 0.1 3 wt % β-1,3 (4)-endoglucanohydrolase, 10-40 wt % silica, 5-20 wt % yeast cell wall or an extract thereof, and 40-80 wt % mineral clay, in amounts relative to each other. In another embodiment, the feed supplement comprises, consists essentially of, or consists of, 0.1 3 wt % β-1,3 (4)-endoglucanohydrolase, 15-30 wt % silica, 5-15 wt % yeast cell wall or an extract thereof, and 50-70 wt % mineral clay, in amounts relative to each other.

In any of the above embodiments, the silica may be provided by diatomaceous earth. In any of the above embodiments, the glucans may be β-glucans. In some embodiments, the β-glucans can be obtained from yeast, or other materials, such as fungi, algae, bacteria, or the like. In any of the above embodiments, the mannans may comprise glucomannan. In some embodiments, the feed supplement does not comprise a separate binder in addition to the components of the feed supplement.

The glucan and mannans (or yeast or yeast cell wall or an extract thereof) can be prepared by a method known to a person of ordinary skill in the art and as further disclosed by the patent documents incorporated herein by reference. Yeast cell wall or an extract thereof may have a feed supplement comprising 0-15% moisture and 85-100% dry matter. The dry matter may comprise 10-65% protein, 0-25% fats, 0-3% phosphorus, 5-30% β-glucan, 5-35% mannans, and 0-15% ash. In an independent embodiment, a commercial source of β-1,3 (4) glucan and glucomannan derived from primary inactivated yeast (*Saccharomyces cerevisiae*) with the following chemical feed supplement can be used: moisture 2-5%; proteins 40-50%; fats 3-8%; phosphorus 0-2%; mannans 10-16%; β-1,3-(4) glucan 10-20%; and ash 2-12%.

In another independent embodiment, the yeast cell wall or an extract thereof comprises moisture 1-7% and dry matter 93-99%, and the dry matter may comprise proteins 18-28%, fats 10-17%, phosphorus 0-2%, mannans 20-30%, β-1,3-(4) glucan 18-28%, and ash 2-5%.

In an independent embodiment of the feed supplement, silica, glucan and mannans, and mineral clay are combined at 1-40%, 0.5-25% and 40-92% by weight, respectively. In an independent embodiment of the feed supplement and/or combination, β-1,3 (4)-endoglucanohydrolase, diatomaceous earth, yeast cell wall or an extract thereof, and mineral clay are combined at 0.05-3%, 1-40%, 1-20% and 40-92% by weight, respectively. In an independent feed supplement and/or combination, β-1,3 (4)-endoglucanohydrolase, diatomaceous earth, yeast cell wall or an extract thereof, and mineral clay are combined at 0.1-3%, 5-40%, 2-15% and 40-80% by weight, respectively. In another independent embodiment of the feed supplement and/or combination, β-1,3 (4)-endoglucanohydrolase, diatomaceous earth, yeast cell wall or an extract thereof, and mineral clay are combined at 0.1-3%, 30-40%, 4-15% and 50-65% by weight, respectively.

The feed supplement may further comprise one or more additional components. Additional components may be used for any desired purpose, such as a substantially biologically inert material added, for example, as a filler, or to provide a desired beneficial effect. For example, the feed supplement may include a carbonate (including a metal carbonate such as calcium carbonate); a trace mineral, such as, but not limited to, chloride, fluoride, iodide, chromium, copper, zinc, iron, magnesium, manganese, molybdenum, phosphorus, potassium, sodium, sulfur, selenium, or a combination thereof; a bulking agent; a micro tracer, such as iron particles coated with a dye; yeast; a carrier; a colorant; a taste enhancer; a preservative; an oil; a vitamin; a sorbic acid or a salt thereof; or a combination thereof. The yeast may be yeast culture, active yeast, a live yeast, a dead yeast, yeast extract, or a combination thereof. The preservative may be benzoic acid or a salt thereof, e.g. sodium benzoate; lactic acid or a salt thereof, e.g. sodium lactate, potassium lactate or calcium lactate; propionic acid or a salt thereof, e.g. sodium propionate; ascorbic acid or a salt thereof, e.g. sodium ascorbate; gallic acid or a salt thereof e.g. sodium gallate; sulfur dioxide and/or sulfites; nitrites; nitrates; choline, or a salt thereof, such as an anion salt of choline, e.g. choline halide, such as chloride, bromide, iodide, fluoride, or choline hydroxide; or any combination thereof. The oil may be mineral oil, corn oil, soybean oil, or a combination thereof. The sorbic acid or salt thereof may be potassium sorbate, sodium sorbate, ammonium sorbate, or a combination thereof. The vitamin may be vitamin A, vitamin $B_1$, vitamin $B_2$, vitamin $B_3$, vitamin $B_5$, vitamin $B_6$, vitamin $B_{12}$, vitamin C, vitamin D, vitamin E, vitamin K, or a combination thereof.

Additionally, or alternatively, the additional components may comprise corn, soybean meal, wheat, wheat fiber, barley, rye, rice hulls, canola, limestone, salt, distillers dried grains with solubles (DDGS), dicalcium phosphate, sodium sesquicarbonate, methionine source, lysine source, L-threonine, biotin, folic acid, kelp, menadione dimethylpyrimidinol bisulfite, calcium aluminosilicate, or any combination thereof.

Additional information concerning feed supplement and/or additional components can be found in PCT application No. PCT/US2015/053439, and U.S. application Ser. Nos. 15/359,342, 14/699,740, 14/606,862, and 62/449,959, each of which is incorporated herein by reference in its entirety.

In some embodiments, the feed supplement does not comprise additional components. In other embodiments, the feed supplement comprises from greater than zero to 40% or more by weight additional components, such as from 0.1% to 40% by weight, or from 0.2% to 35% by weight additional components. In certain embodiments, the feed supplement comprises from 0.1% to 5% by weight additional components, such as from 0.2% to 3% by weight. In other embodiments, the feed supplement comprises from 5% to 20% by weight additional components, such as from 10% to 15% by weight. And in further embodiments, the feed supplement comprises from 20% to 40% by weight additional components, such as from 30% to 35% by weight additional components.

In some embodiments, the feed supplement comprises, consists essentially of, or consists of, silica, mineral clay, glucan, mannans, and endoglucanohydrolase; silica, mineral clay, glucan, mannans, endoglucanohydrolase, micro tracers and mineral oil; silica, mineral clay, glucan, mannans, endoglucanohydrolase, micro tracers, mineral oil, and vitamins; silica, mineral clay, glucan, mannans, endoglucanohydrolase, micro tracers, mineral oil, vitamins, and potassium sorbate; silica, mineral clay, glucan, mannans, endoglucanohydrolase, vitamins, and active yeast; silica, mineral clay, glucan, mannans, endoglucanohydrolase, micro tracers, mineral oil, and active yeast; silica, mineral clay, glucan, mannans, endoglucanohydrolase, and mineral oil; silica, mineral clay, glucan, mannans, endoglucanohydrolase, vitamins, and calcium carbonate; silica, mineral clay, glucan, mannans, endoglucanohydrolase, micro tracers, and wheat fiber; or silica, mineral clay, glucan, mannans, endoglucanohydrolase, and micro tracers. In any of these embodiments, the glucan and mannans may be provided by yeast, yeast cell wall, or yeast cell wall extract.

In some embodiments, the feed supplement does not comprise a peroxide compound. In some embodiments, the feed supplement does not comprise hydrogen peroxide. In some embodiments, the feed supplement does not comprise carbamide peroxide. In some embodiments, the feed supplement does not comprise urea. In some embodiments, the feed supplement does not comprise hydrogen peroxide and urea.

In some embodiments, the feed supplement is administered daily to an animal at time intervals believed or determined to be effective for achieving a beneficial result. The feed supplement may be administered in a single dose daily or in divided doses throughout the day. The amount may be from greater than zero to 500 grams per animal per day, such as from 0.5 grams to 250 grams, from 5 grams to 200 grams, or from 10 grams to 70 grams per animal per day. Alternatively, the feed supplement may be fed or administered in an amount of from greater than zero to 1000 mgs or more per kilogram of the animal's body weight per day, such as from greater than zero to 500 mgs per kilogram body weight. In other embodiments, the feed supplement is fed or administered per weight of animal feed. The feed supplement may be fed or administered in an amount of from greater than zero to 150 kg per ton (2000 pounds) of feed, such as from 0.1 kg to 100 kg per ton of feed. Alternatively, the feed supplement may be fed or administered in an amount of from greater than zero to 20 grams per kilogram of feed, such as from greater than zero to 10 grams of feed.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A composition, comprising:
   granular wheat middlings having a size of from 20 mesh to 80 mesh;
   soybean oil;
   nicarbazin; and
   micro tracers.

2. The composition according to claim 1, comprising from 2 wt % to 4 wt % soybean oil, from 10 wt % to 30 wt % nicarbazin, from greater than zero to 1 wt % micro tracers, and from 65 wt % to 88 wt % wheat middlings.

3. The composition according to claim 1, wherein the granular wheat middlings have:
   an angle of repose of from greater than zero to 40;
   a percent compressibility of from zero to 20%;
   a critical orifice diameter of from greater than zero to 15;
   a composite flow index of from greater than 45 to 100; or
   a combination thereof.

4. The composition according to claim 3, wherein the granular wheat middlings have an angle of repose of from 30 to 40, a percent compressibility of from 15% to 20%, a critical orifice diameter of from 3 to 8, and a composite flow index of from 70 to 85.

5. The composition according to claim 1, wherein the composition has:
   an angle of repose of from greater than zero to 40;
   a percent compressibility of from zero to 20%;
   a critical orifice diameter of from greater than zero to 30;
   a composite flow index of from greater than 45 to 100; or
   a combination thereof.

6. The composition according to claim 5, wherein the composition has an angle of repose of from 30 to 40, a percent compressibility of from 10% to 20%, a critical orifice diameter of from 20 to 30, and a composite flow index of from 55 to 60.

7. The composition according to claim 6, wherein the composition has a composite flow index from 30% to 200% greater than a comparable composition comprising powdered and/or flaky wheat middlings.

8. The composition according to claim 1, further comprising a feed, a feed supplement, or a combination thereof.

9. The composition according to claim 8, wherein the feed supplement comprises *yucca*, *quillaja*, silica, mineral clay, glucan, mannans, or a combination thereof.

* * * * *